United States Patent [19]  
Helwig et al.

[11] Patent Number: 5,066,820  
[45] Date of Patent: Nov. 19, 1991

[54] PROCESS FOR THE PREPARATION OF 1-AMINO-2-CARBOXYANTHRAQUINONES

[75] Inventors: Reinhard Helwig, Gruenstadt; Helmut Hoch, Weisenheim, both of Fed. Rep. of Germany

[73] Assignee: BASF Aktiengesellschaft, Ludwigshafen, Fed. Rep. of Germany

[21] Appl. No.: 551,953

[22] Filed: Jul. 12, 1990

[30] Foreign Application Priority Data

Jul. 28, 1989 [DE] Fed. Rep. of Germany ....... 3925060

[51] Int. Cl.$^5$ ...................... C07C 50/24; C07C 97/24; C09B 1/16
[52] U.S. Cl. .................................... 522/249; 552/251
[58] Field of Search ................................ 552/251, 249

[56] References Cited

U.S. PATENT DOCUMENTS 1,830,838 11/1931 Hopff ................................ 260/376
3,211,754 10/1965 Klingsberg .......................... 552/251
3,541,182 11/1970 Kolliker et al. ...................... 552/249
3,836,548 9/1974 Grelat et al. ........................ 260/376

FOREIGN PATENT DOCUMENTS 1127911 11/1962 Fed. Rep. of Germany .
2622227 12/1977 Fed. Rep. of Germany .
2933531 3/1981 Fed. Rep. of Germany .

OTHER PUBLICATIONS

Morrison & Boyd, *Organic Chemistry*, 1974, pp. 630 and 635.
Bios 987, 13, 3 pages, J. Avery, et al., "Indanthrene Red FBB".

Primary Examiner—C. Warren Ivy
Assistant Examiner—Raymond Covington
Attorney, Agent, or Firm—Oblon, Spivak, McClelland, Maier & Neustadt

[57] ABSTRACT

The preparation of 1-amino-2-carboxyanthraquinones I

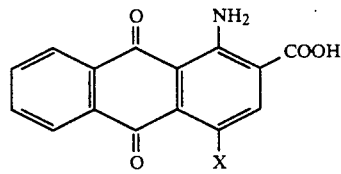

(X denotes hydrogen, chlorine or bromine) by oxidation, under alkaline conditions, of a 1-aminoanthraquinone substituted in the 2-position by an oxidizable carbo-organic radical followed by acidification of the reaction mixture, wherein a 1-amino-2-acetylanthraquinone II

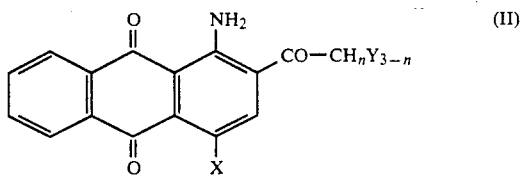

(Y denotes chlorine or bromine and n is equal to 0, 1 or 2) is reacted with a peroxide compound or oxygen as oxidizing agent.

6 Claims, No Drawings

PROCESS FOR THE PREPARATION OF 1-AMINO-2-CARBOXYANTHRAQUINONES

The present invention relates to a novel process for the preparation of 1-amino-2-carboxyanthraquinones of the general formula I

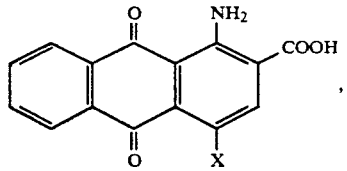

in which X denotes hydrogen, chlorine or bromine, by oxidation, under alkaline conditions, of a 1-aminoanthraquinone substituted in the 2-position by an oxidizable carbo-organic radical, followed by acidification of the reaction mixture.

1-Amino-2-carboxyanthraquinones and 1-amino-2-carboxy-4-halo-anthraquinones are important intermediates in the synthesis of disperse dyes, vat dyes and pigments. As is well known, they can be prepared by a variety of methods, usually by oxidation, under alkaline conditions, of the corresponding anthraquinones carrying an oxidizable carbo-organic radical in the 2-position.

Thus the anthraquinone derivatives I are obtained by oxidation of the corresponding 2-hydroxymethyl compounds with oxidizing agents such as potassium permanganate (DE-A 2,130,699), by oxidation of the corresponding 2-methyl anthraquinones with oxygen under pressure (DE-A 499,994) or by oxidation of 2-methyl-substituted, 2-hydroxymethyl-substituted, 2-formyl-substituted or N-substituted 2-aminomethylanthraquinones with oxygen under strongly basic conditions in water-miscible polar aprotic solvents (DE-A 2,622,227). The oxidation of the 2-acetyl group to a carboxy group using hypochlorites is also known (DE-A 2,933,531).

Of the methods using an acid medium, the oxidation of 1-nitro-2-methylanthraquinone with chromium(IV) compounds is particularly significant (BIOS 987, 13).

However, these processes are unsatisfactory for various reasons, examples of which are the poor yields obtained (e.g. when oxidizing with hypochlorite), the use of organic solvents, the equipment required for operating under pressure or the ensuing contamination of the waste water with heavy metals.

It is thus an object of the present invention to overcome these drawbacks.

Accordingly, we have found a novel process for the preparation of 1-amino-2-carboxyanthraquinones of the general formula I

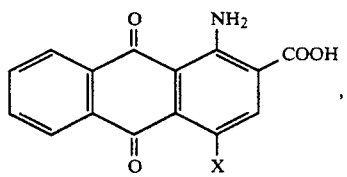

in which X denotes hydrogen, chlorine or bromine, by oxidation, under alkaline conditions, of a 1-aminoanthraquinone substituted in the 2-position by an oxidizable carbo-organic radical, followed by acidification of the reaction mixture, wherein a 1-amino-2-acetylanthraquinone of the general formula II

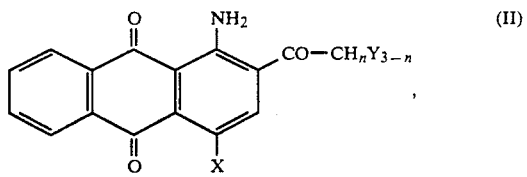

in which Y denotes chlorine or bromine and n is equal to 0, 1 or 2, is reacted with a peroxide compound or oxygen as oxidizing agent.

The 1-amino-2-acetylanthraquinones II used as starting material for the process of the invention are known and are obtained, for example as described in DE-C 1,127,911, by halogenation of 1-amino-2-acetylanthraquinone, which may have been previously halogenated in the nucleus, in concentrated sulfuric acid or acetic acid.

Generally preferred starting materials II are the 1-amino-2-dihaloacetylanthraquinones (n=1), and the compounds which are not substituted in the 4-position (X=H) are of the greatest significance in view of the very important 1-amino-2-carboxyanthraquinone obtainable therefrom.

The preferred oxidizing agents are:
hydrogen peroxide in the form of a 20–40% w/w aqueous solution and
sodium peroxide.

Other suitable oxidizing agents are:
ammonium salts or alkali metal salts of inorganic peroxo-acids such as percarbonates, preferably sodium percarbonate, perborates, preferably sodium perborate, peroxodisulfates, preferably sodium peroxodisulfate,
organic peroxo-acids such as peracetic acid and perbenzoic acid,
oxygen or oxygen-containing gases such as air or mixtures thereof.

The oxidizing agent is preferably used in a molar excess over the anthraquinone derivative II, this excess generally being from 4 to 8 moles, especially 6 to 7 moles.

The base used is an alkali metal or alkaline earth metal hydroxide or alkali metal or alkaline earth metal salt of a weak acid, in particular a carbonate. The hydroxides of sodium and potassium are particularly suitable.

The amount of base added is generally from 100 to 250% w/w and preferably from 150 to 200% w/w of the anthraquinone derivative II. If a base-reacting oxidizing agent is used there is no need to add a base.

The process of the invention is preferably carried out in aqueous solution, but aqueous solutions of organic solvents such as dimethyl formamide, dimethyl acetamide and dimethyl sulfoxide may be used if desired.

The reaction is usually carried out at a temperature of from 20° to 100° C. and preferably from 30° to 70° C.

When run industrially, the process is generally carried out by placing the anthraquinone derivative II in the reactor in an aqueous or alkaline suspension and adding the oxidizing agent with or without added base when the reaction temperature has been reached. Alternatively, the oxidizing agent may be initially placed in the reactor.

If a gaseous oxidizing agent is used, for example air, this is preferably bubbled through the reaction solution at atmospheric pressure. Completion of the reaction may be verified by thin layer chromatography.

Since the reaction and neutralization generally involve gas evolution (oxygen or carbon dioxide), it may be advisable to add small amounts of antifroth agents such as the sodium salts of paraffinsulfonic acids.

The reaction mixture is worked up in the usual way, preferably by precipitation of the end product I by adding an acid, followed by separation and washing.

The anthraquinone obtained is of such a high degree of purity that it is directly suitable for further use, particularly for dye synthesis. Its purity is determined chromatographically in the usual manner.

Compared with prior art processes, the process of the invention is distinguished by its high yields of very pure 1-amino-2-carboxyanthraquinones I and its simplicity of operation.

A particularly preferred application of our process comprises the preparation of unsubstituted 1-amino-2-carboxyanthraquinone, which is an important intermediate in the synthesis of numerous disperse dyes and vat dyes.

EXAMPLES

Preparation of 1-amino-2-carboxyanthraquinones of the formula:

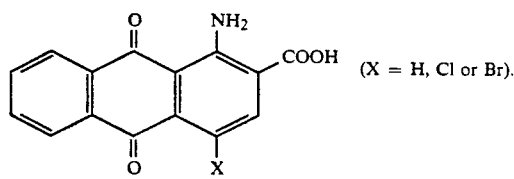

(X = H, Cl or Br).

To a suspension of a moles of a 1-aminoanthraquinone II in b g of water there were added, at 55°–60° C. over 1 hour, c g of 50% w/w caustic soda solution concurrently with d g of an oxidizing agent, after which the mixture was stirred for 2 hours.

Whilst keeping the temperature constant, 75% w/w sulfuric acid was added until the pH was ≦2. The 1-amino-2-carboxyanthraquinone thus precipitated was isolated, washed with water and dried.

Details of these tests and their results are listed in the Table below.

TABLE

| Ex. | a [mole] | 1-amino-anthraquinone II | water b [g] | 50% w/w NaOH soln. [g] | d [g] | oxidizing agent | Yield [g] | Content of I [%] | Absolute yield [%] |
|---|---|---|---|---|---|---|---|---|---|
| 1 | 0.36 | -2-dichloroacetyl- (m.p. 221–223° C.) | 1,200 | 444 | 264 | Perhydrol* | 93 | 93 | 90 |
| 2 | 0.09 | -2-dichloroacetyl- | 375 | — | 40 | sodium peroxide | 22 | 96 | 88 |
| 3 | 0.09 | -2-dichloroacetyl- | 300 | 111 | 2.5 + 60 | sodium peroxide + Perhydrol* | 22 | 94 | 86 |
| 4 | 0.09 | -2-dichloroacetyl- | 300 | 111 | 61 | sodium percarbonate | 22 | 93 | 85 |
| 5 | 0.09 | -2-dichloroacetyl- | 300 | 111 | 100 | sodium perborate | 22 | 93 | 85 |
| 6 | 0.36 | -2-dibromoacetyl- (m.p. 210–213° C.) | 1,200 | 444 | 264 | Perhydrol* | 93 | 93 | 90 |
| 7 | 0.09 | -2-dibromoacetyl- | 375 | — | 40 | sodium peroxide | 22 | 96 | 88 |
| 8 | 0.09 | -2-dibromoacetyl- | 300 | 111 | 2.5 + 60 | sodium peroxide + Perhydrol* | 22 | 94 | 86 |
| 9 | 0.36 | -2-dichloroacetyl-4-chloro- (m.p. 204–206° C.) | 1,200 | 444 | 264 | Perhydrol* | 99 | 93 | 85 |
| 10 | 0.36 | -2-dibromoacetyl-4-chloro- (m.p. 235–236° C.) | 1,200 | 444 | 264 | Perhydrol* | 100 | 95 | 88 |
| 11 | 0.36 | -2-dichloroacetyl-4-bromo- (m.p. 208–211° C.) | 1,200 | 444 | 264 | Perhydrol* | 114 | 92 | 84 |
| 12 | 0.36 | -2-dibromoacetyl-4-bromo- (m.p. 231–234°) | 1,200 | 444 | 264 | Perhydrol* | 114 | 92 | 84 |

*Perhydrol = 30% w/w hydrogen peroxide

We claim:

1. A process for the preparation of a 1-amino-2-carboxyanthraquinone of the general formula I

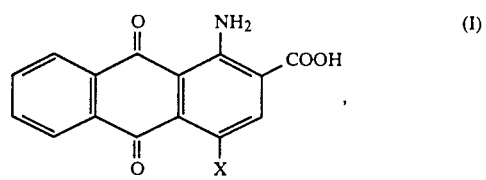

in which X denotes hydrogen, chlorine or bromine, by oxidation, under alkaline conditions, of a 1-aminoanthraquinone substituted in the 2-position by an oxidizable carbo-organic radical followed by acidification of the reaction mixture, wherein a 1-amino-2-haloacetylanthraquinone of the general formula II

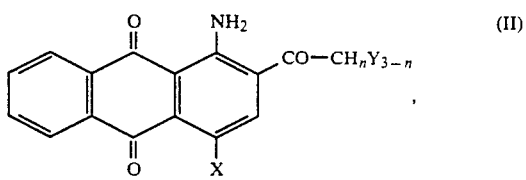

in which Y denotes chlorine or bromine and n is equal to 0, 1 or 2, is reacted with a peroxide compound or oxygen as oxidizing agent.

2. A process as claimed in claim 1, wherein a 1-amino-2-haloacetylanthraquinone of the formula (II) is used in which n is equal to 1.

3. A process as claimed in claim 1, wherein a 1-amino-2-haloacetylanthraquinone of the formula (II) is used in which X denotes hydrogen.

4. A process as claimed in claim 1, wherein the oxidizing agent used is an ammonium or alkali metal percarbonate, perborate or peroxodisulfate, hydrogen peroxide, an alkali metal peroxide, peracetic acid or perbenzoic acid.

5. A process as claimed in claim 1, wherein the reaction is carried out in aqueous solution.

6. A process as claimed in claim 1, wherein the reaction is carried out at a temperature of from 30° to 70° C.

* * * * *